United States Patent

Wade et al.

[11] 4,166,910
[45] Sep. 4, 1979

[54] 3-(NITROGEN CONTAINING HETEROCYCLIC)AMINO) BENZISOTHIAZOLE-1,1-DIOXIDE

[75] Inventors: Peter C. Wade, Pennington, N.J.; B. Richard Vogt, Yardley, Pa.; Thomas P. Kissick, Princeton, N.J.

[73] Assignee: E. R. Squibb & Sons, Inc., Princeton, N.J.

[21] Appl. No.: 924,426

[22] Filed: Jul. 13, 1978

[51] Int. Cl.$^2$ .......................................... C07D 417/12
[52] U.S. Cl. ................... 544/212; 544/322; 544/331; 544/405; 546/270
[58] Field of Search ............... 544/322, 331, 405, 212; 546/270

[56] References Cited

U.S. PATENT DOCUMENTS

| | | | |
|---|---|---|---|
| 2,751,392 | 6/1956 | Grogan et al. | 260/301 |
| 3,225,056 | 12/1965 | Traverso et al. | 260/301 |
| 3,271,406 | 9/1966 | Traverso et al. | 260/301 |
| 3,457,272 | 7/1969 | Crook et al. | 260/301 |

Primary Examiner—Paul M. Coughlan, Jr.
Attorney, Agent, or Firm—Lawrence S. Levinson; Donald J. Barrack

[57] ABSTRACT

Compounds having the formula

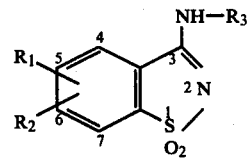

wherein $R_1$ is hydrogen, halogen, alkyl, alkoxy or nitro; $R_2$ is hydrogen, halogen or alkoxy; and $R_3$ is pyridinyl, pyrimidinyl, pyrazinyl, or 1,3,5-triazinyl, have antiinflammatory activity.

6 Claims, No Drawings

3-(NITROGEN CONTAINING HETEROCYCLIC)AMINO) BENZISOTHIAZOLE-1,1-DIOXIDE

RELATED APPLICATIONS

U.S. patent application Ser. No. 799,865, filed May 23, 1977 by Wade and Kissick, now U.S. Pat. No. 4,104,387, issued Aug. 1, 1978, discloses 3-(arylcycloiminoalkyloxy)benzisothiazole 1,1-dioxides and 3-(arylcycloiminoalkylamino)benzisothiazole 1,1-dioxides having antiinflammatory activity.

U.S. patent application Ser. No. 799,879 filed May 23, 1977 by Wade and Kissick, now U.S. Pat. No. 4,104,388, issued Aug. 1, 1978, discloses 3-(cycloimino)-benzisothiazole 1,1-dioxides, 3-(hydroxycycloimino)-benzisothiazole 1,1-dioxides and 3-(arylcycloimino)benzisothiazole, 1,1-dioxides having antiinflammatory activity.

U.S. patent application Ser. No. 875,022, filed Feb. 3, 1978 by Wade and Vogt, discloses [(1,1-dioxo-1,2-benzisothiazol-3-yl)amino] alkanoic acids and esters thereof, and [(1,1-dioxo-1,2-benzisothiazol-3-yl)amino] cycloalkanoic acids and esters thereof, having antiinflammatory activity.

U.S. patent application Ser. No. 875,021, filed Feb. 3, 1978 by Wade, Vogt and Kissick, discloses 2,3-dihydro-1,2,4-triazolo[4,3-b][1,2]benzisothiazol-3-amine, 5,5-dioxides having antiinflammatory activity.

U.S. patent application Ser. No. 875,020, filed Feb. 3, 1978 by Wade and Kissick, discloses 3-(substituted hydrazino)benzisothiazole 1,1-dioxides having the formulas

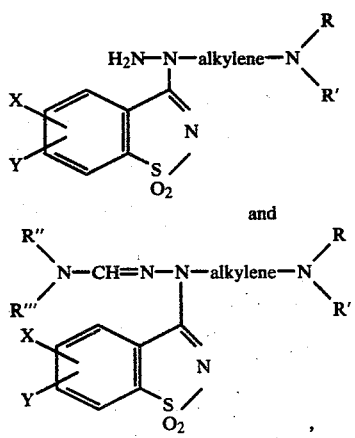

wherein X is hydrogen, halogen, alkyl, alkoxy or nitro, Y is hydrogen, halogen or alkoxy and each of the —NRR groups is dialkylamino or a 5- or 6-membered heterocycle. The compounds have antiinflammatory activity.

U.S. patent application Ser. No. 875,018, filed Feb. 3, 1978 by Wade, Vogt and Kissick, now U.S. Pat. No. 4,108,860, issued Aug. 22, 1978, discloses 1,2,4-triazol[4,3-b][1,2]benzisothiazole, 5,5-dioxides and 3-aryl and 3-alkyl derivates having antiinflammatory activity.

BACKGROUND OF THE INVENTION

U.S. Pat. No. 2,751,392 issued June 19, 1956, discloses, inter alia, compounds having the formula

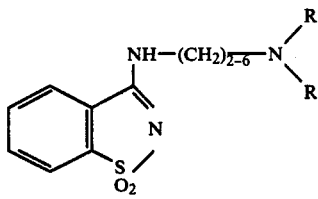

wherein R is alkyl or the —NRR grouping can be a heterocyclic ring. The compounds are said to have analgesic and antihistaminic activity.

U.S. Pat. No. 3,225,056, issued Dec. 21, 1965, discloses, inter alia, 3-(substituted hydrazino)benzisothiazoles having the formula

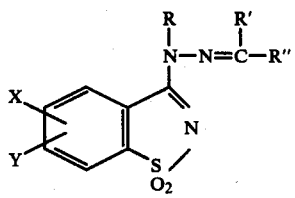

wherein X and Y are hydrogen, halogen, alkyl, alkoxy or trifluoromethyl; R and R' when taken alone are hydrogen; R'' when taken alone is alkyl or alkenyl, or R' and R'' taken together with the carbon atom to which they are attached form a cyclopentyl or cyclohexyl ring; and R and R' when taken together with the

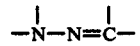

grouping to which they are attached form a heterocyclic ring. The above compounds are said to have hypotensive and diuretic activity.

U.S. Pat. No. 3,271,406 issued Sept 4, 1966, discloses 3-(substituted hydrazino)benzothiazoles having the formula

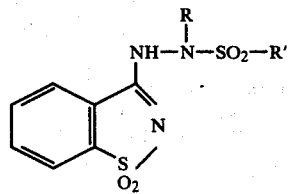

wherein R is hydrogen, alkyl or alkenyl and R' is alkyl, phenyl, α-naphthyl or β-naphthyl. The compounds are said to have hypotensive activity.

U.S. Pat. No. 3,457,272, issued July 22, 1969, discloses, inter alia, N-substituted-1,2-benzisothiazole-3-one, 1,1-dioxides. The compounds are said to exhibit various central nervous system activities.

BRIEF DESCRIPTION OF THE INVENTION

Compounds having the formula

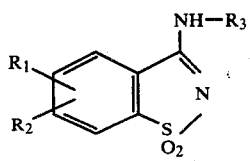

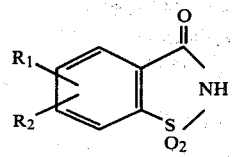

and the pharmaceutically acceptable salts thereof have antiinflammatory activity. In formula I, and through the specification, the symbols are as defined below.

$R_1$ is hydrogen, halogen, alkyl, alkoxy or nitro and $R_2$ is hydrogen, halogen or alkoxy, with the proviso that if $R_2$ is other than hydrogen, $R_1$ and $R_2$ are the same; and $R_3$ is 2-, 3-, or 4-pyridinyl, 2-,4- or 5-pyrimidinyl, 2-pyrazinyl, or 1,3-5-triazin-2-yl(the pyridinyl groups are preferred).

The terms "alkyl" and "alkoxy", as used throughout the specification, refer to groups having 1 to 4 carbon atoms; groups having 1 or 2 carbon atoms are preferred.

The term "halogen" as used throughout the specification, refers to fluorine, chlorine, bromine and iodine; chlorine and bromine are preferred.

DETAILED DESCRIPTION OF THE INVENTION

The compounds of formula I can be prepared by reacting a 3-halo-1,2-benzisothiazole, 1,1-dioxide having the formula

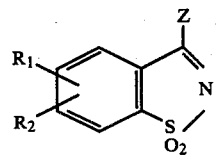

wherein Z is halogen (chlorine being the most preferred) with a primary amine having the formula $$H_2N-R_3 \qquad (III)$$

The reaction can be run in an organic solvent, e.g., dioxane, benzene, dimethylformamide, dimethoxyethane or the like.

The starting materials of formula III are known in the art. Some of the starting materials are commercially available and all of them are readily obtainable via conventional synthetic routes.

The 3-halo-1,2-benzisothiazole, 1,1-dioxides of formula II are also known in the art; see, for example, U.S. Pat. No. 3,225,056, issued Dec. 12, 1965. They can be prepared from the corresponding saccharin compound having the formula

by reaction with thionyl chloride in an inert organic solvent, preferably containing a catalytic amount of dimethylformamide.

The pharmaceutically acceptable salts of the compounds of formula I can be prepared from the corresponding free base using procedures well known in the art. Acid-addition salts are specifically comtemplated, e.g., the hydrohalides (particularly the hydrochloride and hydrobromide), sulfate, nitrate, phosphate, tartrate, maleate, fumarate, citrate, succinate, methanesulfonate, benzenesulfonate, toluenesulfonate and the like.

The compounds of formula I, and the pharmaceutically acceptable salts thereof, can be used to treat inflammation in mammals. Joint tenderness and stiffness (in conditions such as rheumatoid arthritis) can be reduced by these compounds.

The compounds of this invention can be formulated for use as antiinflammatory agents according to accepted pharmaceutical practice in oral dosage forms such as tablets, capsules, elixirs or powders, or in injectable form in a sterile aqueous vehicle. The compounds of this invention can be administered in amounts of 100 milligrams per kilogram of animal body weight per day to 2 grams per kilogram of animal body weight per day, preferably 100 milligrams per kilogram of animal body weight per day to 1 gram per kilogram of animal body weight per day.

The following examples are specific embodiments of this invention.

EXAMPLE 1

N-(2-Pyridinyl)-1,2-benzisothiazol-3-amine, 1,1-dioxide

A solution of 3-chloro-1,2-benzisothiazole, 1,1-dioxide (15.0 g) and 2-aminopyridine (14.0 g) in dioxane (75 ml) is refluxed for 1 hour. The solvent is evaporated and the residue is triturated with hot water. The solid material is filtered out and washed with water. The filter cake is suspended in 400 ml of water, dissolved by adding 20% sodium hydroxide and the product is precipitated by adding concentrated hydrochloric acid to pH 7. The white precipitate is filtered out, washed with water and recrystallized from dimethylformamide (25 ml) ethanol (450 ml) yielding 11.5 g of the title compound, melting point 247°–249° C.

EXAMPLES 2–8

Following the procedure of Example 1, but substituting the compound listed in column I for 3-chloro-1,2-benzisothiazole, 1,1-dioxide and the compound listed in column II for 2-aminopyridine, yields the compound listed in column III.

| Column I | Column II | Column III |
| --- | --- | --- |
| (2) 3,5,6-trichloro-1,2-benzisothiazole, 1,1-dioxide | 3-aminopyridine | 5,6-dichloro-N-(3-pyridinyl)-1,2-benzisothiazol-3-amine, 1,1-dioxide |
| (3) 3-chloro-5-methyl-1,2-benzisothiazole, 1,1-dioxide | 4-aminopyridine | 5-methyl-N-(4-pyridinyl)-1,2-benzisothiazol-3-amine, 1,1-dioxide |

| | Column I | Column II | Column III |
|---|---|---|---|
| (4) | 3-chloro-5,6-dimethoxy-1,2-benzisothiazole, 1,1-dioxide | 2-aminopyrimidine | N-(2-pyrimidinyl)-5,6-dimethoxy-1,2-benzisothiazol-3-amine |
| (5) | 3-chloro-5-nitro-1,2-benzisothiazole, 1,1-dioxide | 4-aminopyrimidine | N-(4-pyrimidinyl)-5-nitro-1,2-benzisothiazol-3-amine, 1,1-dioxide |
| (6) | 3,5-dichloro-1,2-benzisothiazole, 1,1-dioxide | 5-aminopyrimidine | 5-chloro-N-(5-pyrimidinyl)-1,2-benzisothiazol-3-amine, 1,1-dioxide |
| (7) | 3-chloro-5-methyl-1,2-benzisothiazole, 1,1-dioxide | 2-aminopyrazine | 5-methyl-N-(2-pyrazinyl)-1,2-benzisothiazol-3-amine, 1,1-dioxide |
| (8) | 3-chloro-5-ethyl-1,2-benzisothiazole, 1,1-dioxide | 2-amino-1,3,5-triazine | 5-ethyl-N-(1,3,5-triazin-2-yl)-1,2-benzisothiazol-3-amine, 1,1-dioxide |

What is claimed is:
1. A compound having the formula

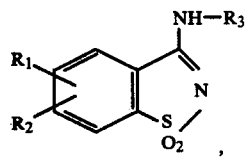

or a pharmaceutically acceptable salt thereof, wherein $R_1$ is hydrogen, halogen, alkyl, alkoxy or nitro and $R_2$ is hydrogen, halogen or alkoxy, provided that if $R_2$ is other than hydrogen, $R_1$ and $R_2$ are the same; and $R_3$ is 2-pyridinyl, 3-pyridinyl, 4-pyridinyl, 2-pyrimidinyl, 4-pyrimidinyl, 5-pyrimidinyl, 2-pyrazinyl, or 1,3,5-triazin-2-yl; wherein the terms "alkyl" and "alkoxy" refer to groups having 1 to 4 carbon atoms.

2. A compound in accordance with claim 1 wherein $R_3$ is 2-pyridinyl, 3-pyridinyl or 4-pyridinyl.

3. A compound in accordance with claim 1 wherein $R_3$ is 2-pyrimidinyl, 4-pyrimidinyl, or 5-pyrimidinyl.

4. A compound in accordance with claim 1 wherein $R_3$ is 2-pyrazinyl.

5. A compound in accordance with claim 1 wherein $R_3$ is 1,3,5-triazin-2-yl.

6. The compound in accordance with claim 2 having the name N-(2-pyridinyl)-1,2-benzisothiazol-3-amine, 1,1-dioxide.